United States Patent
de Paillette

(10) Patent No.: US 6,509,154 B1
(45) Date of Patent: Jan. 21, 2003

(54) PRODUCT COMPRISING AT LEAST A DOUBLE STRANDED RNA COMBINED WITH AT LEAST AN ANTIVIRAL AGENT

(75) Inventor: Evelyne de Paillette, Paris (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/485,086

(22) PCT Filed: Aug. 3, 1998

(86) PCT No.: PCT/FR98/01727

§ 371 (c)(1), (2), (4) Date: Feb. 10, 2000

(87) PCT Pub. No.: WO99/07409

PCT Pub. Date: Feb. 18, 1999

(30) Foreign Application Priority Data

Aug. 4, 1997 (FR) ............................................. 97 09975
Aug. 26, 1997 (FR) ............................................. 97 10644
Sep. 17, 1997 (FR) ............................................. 97 11543

(51) Int. Cl.[7] ........................ C12Q 1/68; C12P 19/34; G01N 33/00; A61K 38/21; C07H 21/02

(52) U.S. Cl. ........................ 435/6; 435/91.1; 436/94; 424/85.4; 536/23.1

(58) Field of Search ................ 435/5, 6, 91.1, 435/91.3, 183; 436/94; 536/22.1, 23.1, 23.5, 23.52, 24.3, 24.33, 25.3; 424/85.4

(56) References Cited

U.S. PATENT DOCUMENTS 4,927,755 A * 5/1990 De Lassauniere et al. . 435/91.1
5,906,980 A * 5/1999 Carter .......................... 514/44

FOREIGN PATENT DOCUMENTS

| EP | 0213921 | 3/1987 |
| EP | 0281380 | 9/1988 |
| EP | 0286224 | 10/1988 |
| EP | 0300680 | 1/1989 |
| EP | 0306347 | 3/1989 |

OTHER PUBLICATIONS

Efficacy of polyadenylic.polyuridylic acid in the treatment of chronic active hepatitis B. Int. J. Immunopharmac. 16, 217–225, Mar. 1994.*

Scnhez–Tapias et al., Interferon in chronic hepatitis C. Lancet 346, suppl. s11, Dec. 1995.*

Copy of Actualite Biologique (9 pages) vol. 40, No. 10, 1006–1014, 1992.

* cited by examiner

*Primary Examiner*—Ethan C. Whisenant
*Assistant Examiner*—Frank Lu
(74) *Attorney, Agent, or Firm*—Bierman, Muserlian and Lucas

(57) ABSTRACT

This invention relates to a method for treating human hepatitis B or C by the combination of a complex of polyadenylic acid and polyuridylic acid and interferon-α.

11 Claims, No Drawings

PRODUCT COMPRISING AT LEAST A DOUBLE STRANDED RNA COMBINED WITH AT LEAST AN ANTIVIRAL AGENT

This application is a 371 of PCT/FR98/01727 filed Aug. 3, 1998.

The present invention relates to a product containing at least one double-stranded RNA (dsRNA) in combination with at least one antiviral agent, preferably an interferon, for therapeutic use, simultaneously, separately or over a period of time, in the treatment of a viral disease. Such a product can be used in particular for the treatment of viral hepatitis.

The Applicant has found that the combination of dsRNA with an antiviral agent, and in particular with an interferon, results in an unexpected synergistic effect in the treatment of viral diseases, in particular the treatment of viral hepatitis.

Therefore a subject of the invention is a product containing at least one dsRNA in combination with at least one antiviral agent for therapeutic use, simultaneously, separately or over a period of time, in the treatment of a viral disease.

By a dsRNA as poly(A) is preferably meant a complex of polyadenylic acid with polyuridylic acid, also known as poly(A)-poly(U) or Poly-adenur®. Other dsRNA'S can be used for the invention, in particular a complex of polyinosinic acid with polycytidylic acid, also known as poly(I)-poly(C), as well as these same complexes modified by the introduction of uridylic acid into the chain of the polycytidylic acid, such as the product Ampligen® manufactured by the HEMISPHERx company (for a description of these products see in particular the European Patent Application EP 0 300 580). The dsRNA used can be, for example, a mixture of dsRNA's as defined above. The dsRNA's are preferably prepared according to the procedure described in U.S. Pat. No. 4,927,755.

In the present Application, by the term "antiviral agent" is meant both an agent acting directly on the virus, such as ribavirin or lamivudine, and an immunomodulatory agent i.e. an agent which weakens or strengthens the immune defenses, such as cyclosporin or an interferon. The antiviral agents combined with the dsRNA can be chosen, for example, from an interferon, such as $\alpha$, $\beta$, or $\gamma$, interferons or consensus interferons, and in particular, an interferon-$\alpha$ (INF-$\alpha$), other lymphokines, such as the interleukins, for example IL 6 or IL 9, ganciclovir, coumermycin A1, lamivudine, ribavirin, vidarabine, dideoxyinosine (DDI), azathioprine, prednisolone or cyclosporin. Preferably, the antiviral agent combined with the dsRNA will be an interferon.

By an interferon-$\alpha$ is meant one or more different interferon-$\alpha$s, such as for example interferons $\alpha$-2a, $\alpha$-2b, $\alpha$-2c, $\alpha$-$n_1$, $\alpha$-$n_3$, or any other analogue having comparable immunological properties. By a consensus interferon is meant, for example, the interferons INF-con1, INF-con2 and INF-con3 (these consensus interferons are described in particular in U.S. Pat. No. 5,372,808 and the Patent Application PCT WO 93/21229).

By simultaneous therapeutic use is meant in the present Application, an administration of more active ingredients by the same route and at the same time. By separate use is meant, in particular, an administration of several active ingredients at approximately the same time by different routes. By therapeutic administration over a period of time is meant the administration of several active ingredients at different times and in particular an administration method according to which the entire administration of one of the active ingredients is completed before the administration of the other or others begins. In this way it is possible to administer one of the active ingredients for several months before administering the other active ingredient or ingredients. In this case, no simultaneous administration occurs.

By viral disease is meant in particular viral hepatitis, and in particular hepatitis B or hepatitis C. The viral hepatitis treated with the product according to the invention can be chronic or acute in nature. Preferably, the product according to the invention is intended for chronic hepatitis.

The invention in particular relates to a product which is characterized in that it comprises:

i) a dsRNA in combination with ii) an antiviral agent for therapeutic use extended over a period of time in the treatment of a viral disease. Preferably, the use of the dsRNA takes place before that of the antiviral agent.

According to a preferred variant of the invention, the invention relates to a product which is characterized in that it comprises:

i) a dsRNA in combination with ii) an interferon for therapeutic use extended over a period of time in the treatment of a viral disease. Preferably, the use of the dsRNA takes place before that of the interferon. Preferably the interferon used will be interferon-$\alpha$.

According to a particular aspect of the invention, the product contains at least one dsRNA in combination with at least one antiviral agent, which can be an immunomudulatory agent and is characterized in that it also contains at least one antiviral agent acting directly on viruses for simultaneous or separate use with the immunomodulatory agents or agents in the treatment of a viral disease. Preferably, the immunomodulatory agent or agents are interferons.

According to another variant of the invention, the product which contains at least one dsRNA in combination with at least one antiviral agent is characterized in that it also contains at least one antiviral agent for therapeutic use which extends over a period of time and takes place before that of the dsRNA in the treatment of a viral disease. Among the other antiviral agents which can be used for this particular variant of the invention, there can be mentioned lymphokines other than interferons such as interleukines, for example, IL 6 or IL 9, ganciclovir, coumermycin A1, lamivudine, ribavirin, vidarabine, dideoxyinosine (DDI), azathioprine, prednisolone or cyclosporin.

Quite particularly, the invention relates to a product characterized by the fact that it comprises:

i) an antiviral agent in combination with ii) a dsRNA, and iii) an interferon, which can be simultaneously or separately combined with an antiviral agent acting directly on the viruses for an administration which is separated in time and carried out in the order indicated above in the treatment of a viral disease, in particular hepatitis B.

Various administration sequences of the dsRNA and the antiviral agent can be envisaged. According to a particular method of the invention, the dsRNA and antiviral are not administered simultaneously. Preferably, the dsRNA is administered before the antiviral agent with which it is combined. The treatment with the dsRNA extends preferably over a period of 1 to 12 months or more, for example 6 months, and followed by an administration of the antiviral agent over an equivalent or different period of time.

A subject of the invention is also pharmaceutical compositions containing, as active ingredient, a product according to the invention, i.e. a product containing at least one dsRNA in combination with at least one antiviral agent, preferably an interferon, in combination with appropriate excipients or supports for a therapeutic use simultaneously, separately or over a period of time, in the treatment of viral diseases.

Preferably, the viral disease treated by the pharmaceutical products and compositions according to the invention will be viral hepatitis, such as hepatitis A, B, C or G or "non A, non B, non C, non G" hepatitis i.e. hepatitis of a type other than types A, B, C or G. The pharmaceutical products and compositions according to the invention are intended particularly for the treatment of hepatitis B or hepatitis C. Furthermore, the viral hepatitis treated with the pharmaceutical products and compositions according to the invention can take the form of acute or chronic viral hepatitis and will preferably consist of chronic viral hepatitis. The viral hepatitis treated with the pharmaceutical products and compositions according to the invention will particularly preferentially be chronic hepatitis B or C.

The pharmaceutical compositions containing a product according to the invention can be in the form of a solid, for example powders, granules, tablets, capsules, liposomes or suppositories. Appropriate solid supports can be, for example, calcium phosphate, magnesium stearate, talc, sugars, lactose, dextrin, starch, gelatin, cellulose, methylcellulose, sodium carboxymethylcellulose, polyvinylpyrrolidine or wax.

The pharmaceutical compositions containing a product according to the invention can also be presented in the form of a liquid, for example solutions, emulsions, suspensions or syrups. Appropriate liquid supports can be, for example, water, organic solvents, such as glycerol or glycols, as well as their mixtures, in various proportions, in water.

Finally, the invention relates to the use of a product according to the invention, i.e. a product containing at least one dsRNA and at least one antiviral agent, to manufacture a medicament intended for the treatment of viral diseases, and in particular of viral hepatitis. Preferably, the viral disease treated by the product according to the invention will be hepatitis B or hepatitis C. Preferably, the antiviral agent combined with the dsRNA is an interferon. An interferon-$\alpha$ (INF-$\alpha$) will be quite particularly preferred.

The administration method of the product according to the invention is chosen from conventional administration methods. For example, the administration of the dsRNA can take place, for example, by topical, oral or parenteral route, by intramuscular or intravenous injection, or by subcutaneous route. Similarly, the antiviral agents can be administered by the same routes. For each of these compounds, a person skilled in the art will select the most appropriate administration method.

The administration dose envisaged for the medicament according to the invention is between 0.1 mg and 10 g per administration, depending on the type of active compound used.

In the case of dsRNA, in particular that of poly(A)-poly(U), a dose can preferably be envisaged between 10 mg and 3 g per dose. The product can be administered daily or several times a week. For example, a dose of between 15 mg and 1.5 g can be administered, preferably of the order of 50 to 300 mg two or three times per week.

The dose of interferon will in theory be that usually used by a person skilled in the art, and preferably between 0.5 and 60 million international units per dose. In the case of INF-$\alpha$, for example, the dose can be between 1 and 50 million units, preferably between 1 and 10, and in particular between 3 and 6 million units. Furthermore, administration can be daily or take place several times a week. In particular, two or three administrations can be administered per week. For example, it is possible to choose to administer between 3 and 6 million units two or three times per week.

According to another variant of the invention, it is also possible to precede the treatment with dsRNA by a treatment with an antiviral agent. For example, one could administer an interferon, lamivudine or ribavirin during the first period, the dsRNA during a second period and finally during a third period, an interferon optionally combined with at least one antiviral agent, such as ribavirin or lamivudine. The interferon used for the treatment will preferably be an INF-$\alpha$.

To choose the administration methods and doses, a person skilled in the art could also usefully consult the following article (and the references cited therein): Daniel Dhumeaux, *La revue du practicien*, 45 pp 2519–2522 (1995).

Unless otherwise defined, all the technical and scientific terms used here have the same meanings as those generally understood by the ordinary specialist in the field to which this invention belongs. Similarly, all the publications, patent applications, all patents and all other references mentioned here are incorporated by way of reference.

CLINICAL PROPERTIES OF THE PRODUCTS ACCORDING TO THE INVENTION

Example 1

A group of ten patients suffering from hepatitis C was treated successively with poly(A)poly(U) with a molecular weight of about 250,000 to 1,500,000 and then with interferon. The treatment was carried out as follows:

initially, the patients received twice weekly administrations of a dose of 150 mg of poly(A)poly(U) administered by intravenous route for 24 weeks;

after this initial treatment, the patients received a dose of 3 million units of interferon administered by intravenous route 3 times per week for 24 weeks.

After this two-stage treatment, a remission of the disease was observed in 6 of the patients, a remission followed by a relapse in a seventh patient and the treatment had no effect in only three of the patients.

By way of comparison, a treatment consisting of interferon alone produced remission in only 20 to 30% of the cases treated (cf. Daniel Dhumeaux, *La revue du practicien*, 45 pp 2519–2522 (1995).

Example 2

Two groups of patients suffering from active chronic hepatitis B, the first group consisting of 42 patients (group A), the second consisting of 44 patients (group B) received the following treatments, starting on the same date:

the patients in group A received a dose of 150 mg of poly(A)-poly(U) administered by intravenous route twice weekly for 24 weeks and then a dose of 6 million units of IFN-$\alpha$ administered by subcutaneous route 3 times per week for the next 24 weeks;

the patients in group B received no treatment for the first 24 weeks and then received 6 million units of IFN-$\alpha$ administered by subcutaneous route 3 times per week for the next 24 weeks.

The presence of the DNA of the HBV virus and an HBe serum test were determined 24, 48 and 72 weeks after the date when the treatment with poly(A)-poly(U) was started. The results, expressed in terms of the percentage of patients who responded to the treatment, are summarized in the table below:

|  | After 24 weeks | | After 48 weeks | | After 72 weeks | |
| --- | --- | --- | --- | --- | --- | --- |
| Criterion | Group A | Group B | Group A | Group B | Group A | Group B |
| Absence of DNA of HBV virus or reduction of more than 50% | 40% | 37% | 94%+ | 58%+ | 71%* | 39%* |
| HBe serum test | 14% | 7% | 29% | 14% | 33%** | 9%** |

+p = 0.001;
*p = 0.02
**p = 0.006

Conclusion: in the patients suffering from active, chronic hepatitis B, pre-treatment with poly(A)-poly(U) before the treatment with INF-α had the result of increasing the response rate to the 6-month treatment with INF-α and reduced the number of relapses after this treatment.

What is claimed is:

1. A method of treating viral hepatitis selected from the group consisting of hepatitis B and hepatitis C in humans comprising administering to humans in need thereof over a first period of time a therapeutically effective amount of a complex of polyadenylic acid and polyuridylic acid having a molecular weight of 250,000 to 1,500,00 and then administering over a second period of time a therapeutically effective dose of interferon-α.

2. The method of claim 1 wherein the poly(A)poly(U) with a molecular weight of 250,000 to 1,500,000 is administered over a period of at least 1 to 12 months and, afterwards, the interferon-α is administered over an equivalent period of time.

3. The method of claim 1 wherein the doses of complex of poly(A)poly(U) with a molecular weight of 250,000 to 1,500,000 each consist of 50 to 300 mg of the said complex.

4. The method of claim 3 wherein 50 to 300 mg of the poly(A)poly(U) with a molecular weight of 250,000 to 1,500,000 are administered two or three times per week of treatment by said complex.

5. The method of claim 1 wherein the doses of interferon-α consist of 1 to 10 million international units of said interferon.

6. The method of claim 5 wherein 1 to 10 million international units of interferon-α are administered two or three times per week of treatment by the interferon-α.

7. The method of claim 6 wherein 3 to 6 million international units of interferon-α are administered two or three times per week by the interferon-α.

8. A method according to claim 1 wherein 50 to 300 mg of complex of poly(A)poly(U) with a molecular weight of 250,000 to 1,500,000 are administered two or three times per week of treatment by said complex and, afterwards, 3 to 6 million international units of interferon-α administered two or three times per week of treatment by the interferon-α.

9. A method of claim 1 wherein the hepatitis treated is hepatitis B.

10. A method of claim 1 wherein the hepatitis treated is hepatitis C.

11. The method of claim 1 wherein the first period of time is a period of 1 to 12 months.

* * * * *